United States Patent [19]

Tominaga et al.

[11] Patent Number: 5,478,560
[45] Date of Patent: Dec. 26, 1995

[54] EXTERNAL DERMATOLOGICAL COMPOSITION

[75] Inventors: Naoki Tominaga; Ito Kenzo; Yoshimaru Kumano, all of Yokohama, Japan

[73] Assignee: Shiseido Company Ltd., Tokyo, Japan

[21] Appl. No.: 161,447

[22] Filed: Dec. 6, 1993

Related U.S. Application Data

[63] Continuation of Ser. No. 861,789, filed as PCT/JP90/01348, Oct. 19, 1990, abandoned.

[51] Int. Cl.⁶ .............................. A61K 7/00; A61K 38/04
[52] U.S. Cl. ................... 424/401; 514/2; 514/847
[58] Field of Search ...................... 424/401; 514/2, 514/847

[56] References Cited

U.S. PATENT DOCUMENTS

| | | | |
|---|---|---|---|
| 4,804,674 | 2/1989 | Curtis-Prior | 514/561 |
| 5,019,558 | 5/1991 | Cehovic | 514/183 |
| 5,053,230 | 10/1991 | Gazzani | 424/582 |
| 5,100,655 | 3/1992 | Takano | 424/63 |

FOREIGN PATENT DOCUMENTS

| | | | |
|---|---|---|---|
| 204017 | 12/1986 | European Pat. Off. . | |
| 1382068 | 11/1964 | France . | |
| 2273514 | 1/1976 | France . | |
| 8059038 | 12/1981 | Japan | 424/70 |
| 64-19051 | 1/1989 | Japan . | |
| 64-47707 | 2/1989 | Japan . | |

*Primary Examiner*—Thurman K. Page
*Assistant Examiner*—Sally Gardner
*Attorney, Agent, or Firm*—Foley & Lardner

[57] ABSTRACT

An external dermatological composition comprising a salt of L-arginine-L-aspartic acid and a pharmacologically acceptable carrier therefor.

4 Claims, No Drawings

EXTERNAL DERMATOLOGICAL COMPOSITION

This application is a continuation of U.S. application Ser. No. 07/861,789 filed as PCT/JP90/01348, Oct. 19, 1990, abandoned.

TECHNICAL FIELD

The present invention relates to an external dermatological composition comprising a salt of L-arginine-L-aspartic acid and having effects of preventing the skin from drying and further, activating the skin.

BACKGROUND ART

A dermatological composition containing various humectants incorporated therein for preventing the skin from drying and a dermatological composition containing various vitamins and extracts of organisms incorporated therein for activating aging skin have been proposed, but a dermatological composition providing a combination of these effects has not been proposed in the art.

DISCLOSURE OF INVENTION

Accordingly, an object of the present invention is to provide an external dermatological composition capable of not only preventing the skin from drying but also activating the skin.

Other objects and features of the present invention will be apparent from the following description.

In accordance with the present invention, there is provided an external dermatological composition comprising a salt of L-arginine-L-aspartic acid and a pharmacologically acceptable carrier therefor.

BEST MODE FOR CARRYING OUT THE INVENTION

The present inventors have made extensive and intensive studies with a view to developing a compound capable of not only preventing the skin from drying but also activating the skin, and as a result, found that a L-arginine-L-aspartate (i.e., a salt of L-arginine-L-aspartic acid) provides these effects, and thus completed the present invention.

The L-arginine-L-aspartate usable in the present invention is a salt comprising L-arginine produced by a chemical synthesis or a biosynthesis through the use of a microorganism or the like, and L-aspartic acid produced in the same manner as that used in the production of L-arginine, in a proportion of 1:1.

The amount of the L-arginine-L-aspartate incorporated according to the present invention is 0.0001 to 10% by weight, preferably 0.01 to 1% by weight, based on the total amount of the external dermatological composition.

The pharmacologically acceptable carrier incorporated in the external dermatological composition of the present invention may be any carrier conventionally used in the art for the external dermatological composition. Examples thereof include water, lower alcohols, higher alcohols, polyhydric alcohols, monosaccharides, disaccharides, polysaccharides, hydrocarbon oils, fats and oils, waxes, fatty acids, silicone oils, nonionic surfactants, ionic surfactants, silicone surfactants, high-molecular weight compounds, and water-based mixtures and emulsion mixtures of carriers optionally selected from the above-mentioned carriers.

If necessary, the external dermatological composition of the present invention may further contain various components conventionally used in cosmetics and drugs, etc., as long as the effect of the present invention is not impaired thereby. Examples of such components include vitamin A such as vitamin oil, retinol and retinol acetate; vitamin $B_2$ such as riboflavin, butyric riboflavin and flavin adenine dinucleotide; vitamin Be such as pyridoxin hydrochloride and pyridoxin dioctanoate, vitamin C such as L-ascorbic acid, L-ascorbic acid dipalmitic acid ester, L-ascorbic acid-2-sodium sulfate, L-ascorbic acid phosphoric acid ester, DL-α-tocopherol-L-ascorbic acid phosphoric acid diester dipotassium, pantothenic acids such as calcium pantothenate, D-pantothenyl alcohol, panthothenyl ethyl ether and acetylpanthotheyl ethyl ether, vitamin D such as ergocalciferol and cholecalciferol; nicotinic acids such as nicotinic acid, nicotinic acid amide and benzyl nicotinate; vitamin E such as α-tocopherol, tocopherol acetate, DL-α-tocopherol nicotinate and DL-α-tocopherol cinnamate; vitamins such as vitamin P and biotin; oils such as avocado oil, palm oil, peanut oil, beef tallow, rice bran oil, JoJoba oil, evening primrose oil, carnauba wax, lanolin, liquid paraffin, squalane, isostearyl palmitate, isostearyl alcohol and glycerol tri-2-ethylhexanoate; humectants such as glycerol, sorbitol, polyethylene glycol, 1,3-butylene glycol, collagen, hyaluronic acid, chondroitin sulfate and sodium dextran sulfate; ultraviolet absorbers such as amyl p-dimethylaminobenzoate, octyl methoxycinnamate, 4-tert-butyl-4-methoxy-dibenzoylmethane, glyceryl di-p-methoxycinnamate mono-2-ethyl hexanoate, 2-hydroxy-4-methoxybenzophenone, sodium 2-hydroxy-4-methoxybenzophenone-5-sulfonate, urocanic acid and ethyl diisopropylcinnamate; antioxidants such as sodium erythorbate and p-hydroxyanisole; surfactants such as sodium stearylsulfate, diethanolamine cetylsulfate, cetyltrimethylammonium saccharin, polyethylene glycol isostearate, polyoxyethyleneoctyldodecyl alcohol, sorbitan monoisostearate, polyoxyethylenehydrogenated castor oil, glyceryl arachidate, diglycerol diisostearate and phospholipid; preservatives such as methyl p-oxybenzoate, ethyl p-oxybenzoate and butyl p-oxybenzoate; antiphlogistics such as glycyrrhizinic acid derivatives, glycyrrhezinic acid derivatives, salicylic acid derivatives, hinokitiol, zinc oxide and allantoin; beauty whitening agents such as placental extract, glutathione and saxifrage extract; extracts from phellodendron, coptis rhizome, lithospermum, plony root, swertia herb, birch, sage, loquat, carrot, aloe, mallow, iris, grapes, coix seed, dishcloth gourd, lily, saffron, cnidium rhizome, ginger, Saint-John's-wort, ononis, rosemary and garlic, activating agents such as royal jelly, photosensitive principle, cholesterol derivatives and infant bovine blood extract; blood flow quickening agents such as γ-oryzanol; antiseborrheic agents such as sulfur and thianthol; thickeners such as carboxyvinyl polymer, carboxymethyl cellulose and carboxyhydroxypropyl cellulose; perfumes; water; alcohols; coloring materials such as titanium yellow, carthamin and safflower red, and powdery resins such as polyethylene and nylon.

The dosage form of the external dermatological composition according to the present invention is not limited. Examples thereof include solubilized preparations such as oil preparations and a beauty wash, emulsions such as milky lotions and creams, and ointments, dispersions and powders.

Although the amount applied of the external dermatological composition according to the present invention is not particularly limited, preferably the external dermatological composition is applied twice a day in an amount of 1.5 to 2 ml each time for the beauty wash, 1 to 1.5 ml each time for the milky lotion, and about 0.2 g each time for the cream.

EXAMPLES

The present invention will now be further described by, but is by no means limited to, the following Examples. The amount of incorporation is expressed in terms of % by weight.

Example 1: Cosmetic Liquid

| (1) L-arginine-L-aspartate | 5.0 |
|---|---|
| (2) tocopherol acetate | 0.01 |
| (3) glycerol | 4.0 |
| (4) 1,3-butylene glycol | 4.0 |
| (5) ethanol | 7.0 |
| (6) polyoxyethylene (50 mol) oleyl alcohol ether | 0.5 |
| (7) methyl p-oxybenzoate | 0.2 |
| (8) citric acid | 0.05 |
| (9) sodium citrate | 0.1 |
| (10) perfume | 0.05 |
| (11) purified water | balance |

(Preparation)

Citric acid, sodium citrate, glycerol, 1,3-butylene glycol and L-arginine-L-aspartate were dissolved in the purified water. Separately, polyoxyethylene oleyl alcohol ether, tocopherol acetate, perfume and methyl p-oxybenzoate were dissolved in ethanol. The resultant solution was added to the purified water solution for solubilization, and the mixture was filtrated to give a cosmetic liquid.

Example 2: Cream

| (1) cetostearyl alcohol | 3.5 |
|---|---|
| (2) squalane | 40.0 |
| (3) beeswax | 3.0 |
| (4) reduced lanolin | 5.0 |
| (5) ethyl p-oxybenzoate | 0.3 |
| (6) polyoxyethylene (20 mol) sorbitan monopalmitate | 2.0 |
| (7) monoglyceride stearate | 2.0 |
| (8) sodium N-stearoyl glutamate | 0.5 |
| (9) 2-hydroxy-4-methoxybenzophenone | 1.0 |
| (10) retinol acetate | 2.0 |
| (11) evening primrose oil | 0.05 |
| (12) perfume | 0.03 |
| (13) L-arginine-L-aspartate | 0.01 |
| (14) 1,3-butylene glycol | 5.0 |
| (15) polyethylene glycol 1500 | 5.0 |
| (16) purified water | balance |

(Preparation)

The components (1), (2), (3), (4), (5), (6), (7), (8), (9), (10), (11) and (12) were heat-dissolved in each other, and the solution was added to the components (13), (14), (15) and (16) heated to 75° C. with stirring. The mixture was treated by a homomixer to reduce the size of emulsified particles, and rapidly cooled while stirring to give a cream.

Example 3: Milky Lotion

| (1) stearic acid | 1.5 |
|---|---|
| (2) cetyl alcohol | 0.5 |
| (3) beeswax | 2.0 |
| (4) polyoxyethylene (10 mol) monooleate | 1.0 |
| (5) octyl methoxycinnamate | 2.0 |
| (6) magnesium L-ascorbate phosphate | 0.2 |
| (7) L-arginine-L-aspartate | 1.0 |
| (8) sodium hyaluronate | 0.1 |
| (9) triethanolamine | 0.75 |
| (10) glycerol | 7.0 |
| (11) ethanol | 3.0 |
| (12) ethyl p-oxybenzoate | 0.3 |
| (13) perfume | 0.03 |
| (14) purified water | balance |

(Preparation)

The perfume was added to ethanol, to dissolve the perfume (alcohol phase). The glycerol, triethanolamine, sodium hyaluronate, DL-α-tocopherol-L-ascorbic acid phosphoric acid diesterdipotassium and L-arginine-L-aspartate were added and dissolved in the purified water, and the solution was maintained at 70° C. (aqueous phase). The other components were mixed and heat-dissolved with each other, and the solution was maintained at 70° C. (oil phase). The oil phase was added to the aqueous phase to conduct a preliminary emulsification, and the mixture was homogeneously emulsified by a homomixer.

The emulsion was added to the alcohol phase while stirring, and the mixture was cooled to 30° C. while stirring to give an emulsified solution.

Example 4: Foam Mask

| (1) L-arginine-L-aspartate | 0.5 |
|---|---|
| (2) 1,3-butylene glycol | 5.0 |
| (3) glycerol | 7.0 |
| (4) methyl p-oxybenzoate | 0.1 |
| (5) potassium hydroxide | 0.15 |
| (6) stearic acid | 0.5 |
| (7) myristic acid | 1.0 |
| (8) batyl alcohol | 1.5 |
| (9) polyoxyethylene (60 mol)-hydrogenated castor oil | 3.0 |
| (10) perfume | 0.05 |
| (11) liquified petroleum gas | 6.0 |
| (12) dimethyl ether | 3.0 |
| (13) purified water | balance |

(Preparation)

The components (1), (2), (3), (4) and (5) were added and heat-dissolved in the component (13) at 70° C., and a solution prepared by heat-dissolving the components (6), (7), (8), (9) and (10) with each other at 75° C. were added thereto. The mixture was thoroughly stirred and then cooled, and thereafter, the mixture was packed into a vessel, and the components (11) and (12) were finally packed into the vessel to give a foam mask.

Example 5: Ointment

| (1) L-arginine-L-aspartate | 0.5 |
|---|---|
| (2) tocopherol acetate | 1.0 |
| (3) retinol palmitate | 0.5 |
| (4) stearyl alcohol | 18.0 |
| (5) Japan wax | 20.0 |
| (6) polyoxyethylene (20 mol) monooleate | 0.25 |
| (7) glycerol monostearate | 0.3 |
| (8) petrolatum | 40.0 |
| (9) purified water | balance |

(Preparation)

The L-arginine-L-aspartate was added to the purified water, and the solution was maintained at 70° C. (aqueous phase). The remaining components were mixed and dissolved in each other at 70° C. (oil phase). The oil phase was added to the aqueous phase, and the mixture was homogeneously emulsified by a homomixer and then cooled to give an ointment.

Evaluation Example

The moisture retentive property of the L-arginine-L-aspartate was evaluated through the calculation of a water evaporation rate constant. Specifically, a 10% aqueous solution of L-arginine-L-aspartate was dropped on a filter paper. The change of weight was measured with the elapse of time by a precision balance and a personal computer, to calculate the water evaporation rate constant. The results are given in Table 1. The smaller the water evaporation rate constant, the less the evaporation and the better the moisture retention property.

TABLE 1

| Moisture Retention Effect of L-Arginine-L-Aspartate | |
|---|---|
| | water evaporation rate constant (mg/min) |
| Ion-exchanged water | 43.1 ± 3.6 |
| L-arginine-L-aspartate | 27.4 ± 1.9 |

(n = 3, average ± standard deviation)

It is apparent that the L-arginine-L-aspartate has the effect of preventing an evaporation of water and retaining moisture.

The activating effect of the L-arginine-L-aspartate was evaluated by a cell cultivation technique. Human fibroblast (derived from the skin of a 69 year-old person) was inoculated on a multi-well plate such that the number of cells were $24.0 \times 10^3$ cell/well. Thereafter, 1 ppm of L-arginine-L-aspartate was added thereto, and cultivation was conducted for 5 days. Then the proliferated cells were quantitatively determined by a method proposed by C. Labarca et al. (C. Labarca and K. Paigen, Analytical Biochemistry, 102, 344–352, 1980). The results are given in Table 2.

TABLE 2

| Cell Proliferation Accelerating Effect of L-Arginine-L-Aspartate | |
|---|---|
| | Number of proliferated cell ($10^3$ cells/well) |
| L-arginine-L-aspartate not added | 42.3 ± 0.5 |
| L-arginine-L-aspartate added | 46.7 ± 0.6 |

(n = 3, average ± standard deviation)

It is apparent that the L-arginine-L-aspartate accelerates the proliferation of cells.

From the above-mentioned results, it is apparent that the L-arginine-L-aspartate has not only a moisture retention property but also a skin activating effect.

We claim:

1. A method for preventing skin from drying and for accelerating the proliferation of skin cells by treating the skin with an external dermatological composition comprising a salt of L-arginine-L-aspartic acid and a pharmacologically acceptable carrier thereof, wherein the content of the salt of L-arginine-L-aspartic acid is 0.0001 to 10% by weight.

2. A method for accelerating the proliferation of skin cells by treating the skin with an external dermatological composition comprising a salt of L-arginine-L-aspartic acid and a pharmacologically acceptable carrier thereof, wherein the content of the salt of L-arginine-L-aspartic acid is 0.0001 to 10% by weight.

3. A method as claimed in claim 2, wherein the content of the salt of L-arginine-L-aspartic acid is 0.01 to 1% by weight.

4. A method as claimed in claim 1, wherein the content is 0.01 to 1% by weight.

* * * * *